US006454925B1

United States Patent
Nakanishi et al.

(10) Patent No.: US 6,454,925 B1
(45) Date of Patent: Sep. 24, 2002

(54) DEVICE FOR ELECTROPHORESIS AND COMPONENT THEREFOR

(75) Inventors: Hiroaki Nakanishi, Nara; Takuro Izuo, Hiroshima, both of (JP)

(73) Assignee: Shimadzu Corporation, Kyoto (JP)

( * ) Notice: Subject to any disclaimer, the term of this patent is extended or adjusted under 35 U.S.C. 154(b) by 87 days.

(21) Appl. No.: 09/591,087

(22) Filed: Jun. 9, 2000

Related U.S. Application Data

(63) Continuation-in-part of application No. 09/138,835, filed on Aug. 24, 1998, now abandoned.

(30) Foreign Application Priority Data

Aug. 25, 1997 (JP) .............................................. 9-244616

(51) Int. Cl.[7] .......................... G01N 27/26; G01N 30/02
(52) U.S. Cl. ...................... 204/603; 204/616; 204/612; 422/70
(58) Field of Search ................................. 204/451, 452, 204/456, 466, 461, 606, 616, 603, 612; 356/344; 422/70; 436/161

(56) References Cited

U.S. PATENT DOCUMENTS

| | | | |
|---|---|---|---|
| 4,908,112 A | 3/1990 | Pace | 210/198.2 |
| 5,035,863 A | 7/1991 | Finlan | 422/82.05 |
| 5,917,608 A | 6/1999 | Naya et al. | 356/445 |

*Primary Examiner*—Jill Warden
*Assistant Examiner*—Alex Noguerola
(74) *Attorney, Agent, or Firm*—Beyer Weaver & Thomas LLP

(57) ABSTRACT

A device for electrophoresis includes a component formed with a pair of planar members such as glass substrates joined together one on top of the other such that a capillary is formed by a groove on the surface of at least one of these planar members. A metallic film is disposed on the inner wall of at least a portion of the capillary, and a transparent prism is provided over this metallic film. Electrodes are inserted both on the same side of the metallic film into the capillary for providing a voltage difference between them for causing migration of a liquid in the capillary for electrophoresis without subjecting the metallic film to the applied voltage. A light source is disposed to cause light to be made incident through the prism onto the metallic film at angles of incidence greater than the critical angle for total reflection and including the resonance angle for excitation of surface plasmons on the metallic film. A detector detects reflected light and a data processor receives detection signals from the detector and obtains a resonance curve for optical excitation of surface plasmons on the metallic film. Data on separation times of known components in electrophoresis are stored. As changes in the resonance curve are detected, components of a sample migrating through the capillary are analyzed.

18 Claims, 5 Drawing Sheets

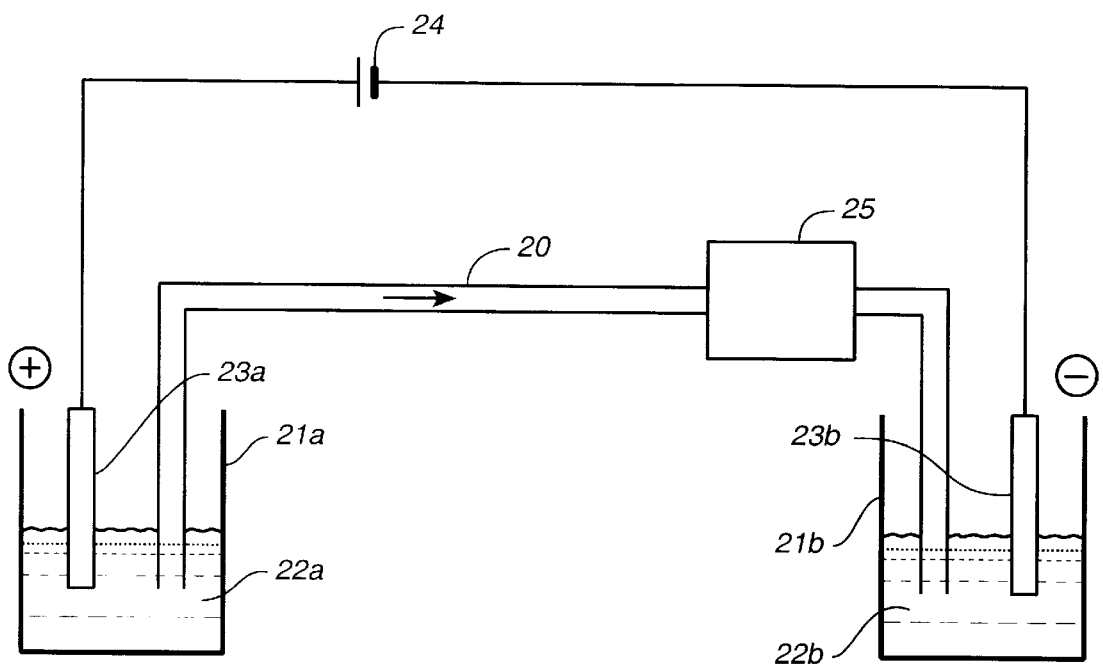
FIG._1 (PRIOR ART)
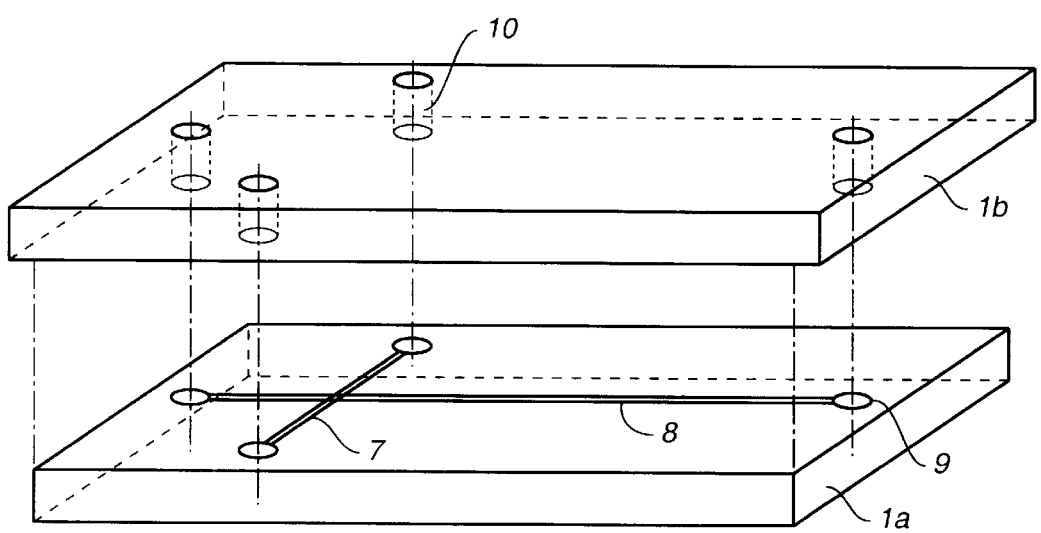
FIG._2 (PRIOR ART)

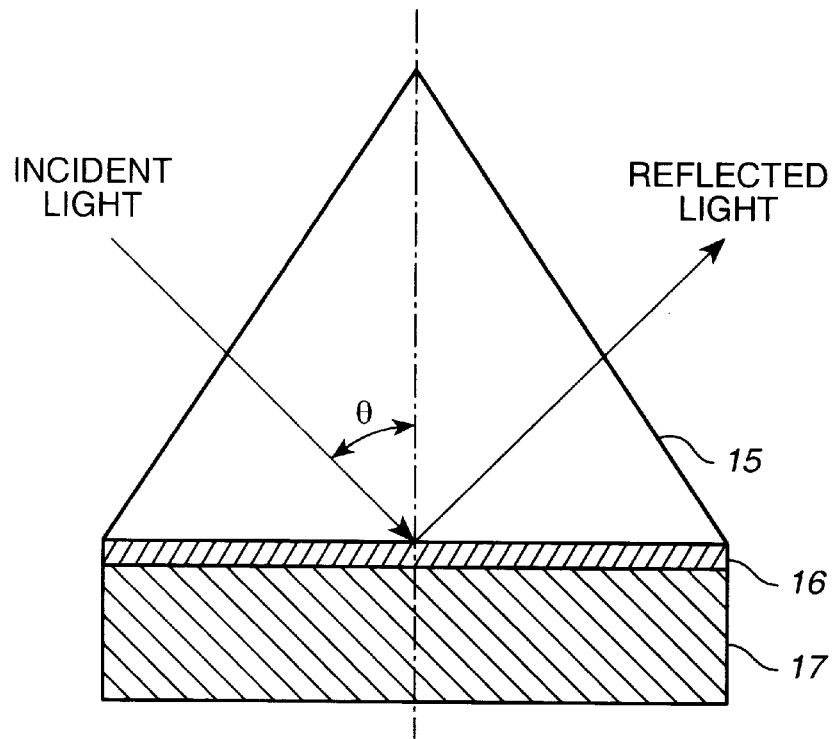
FIG._3A
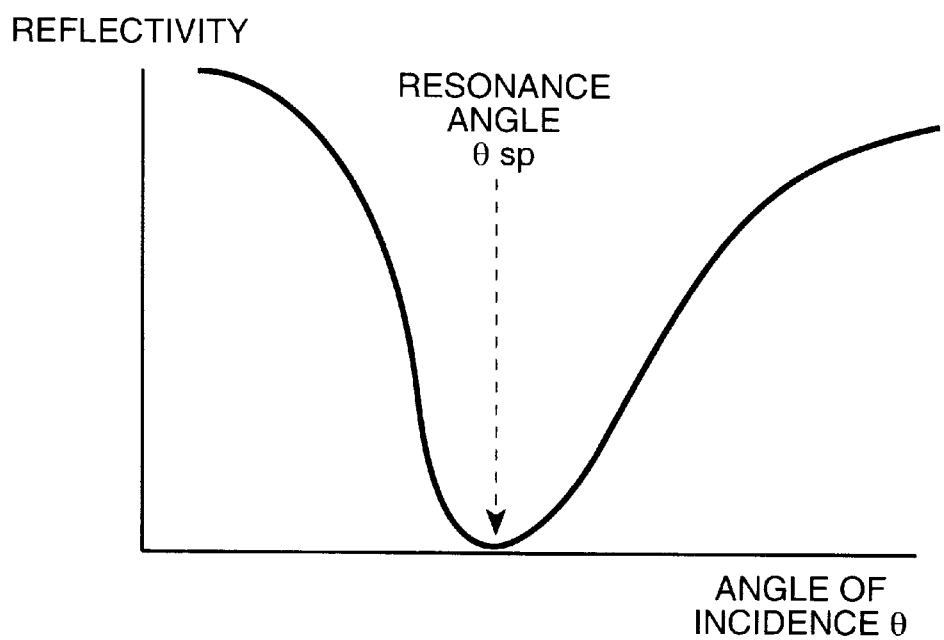
FIG._3B

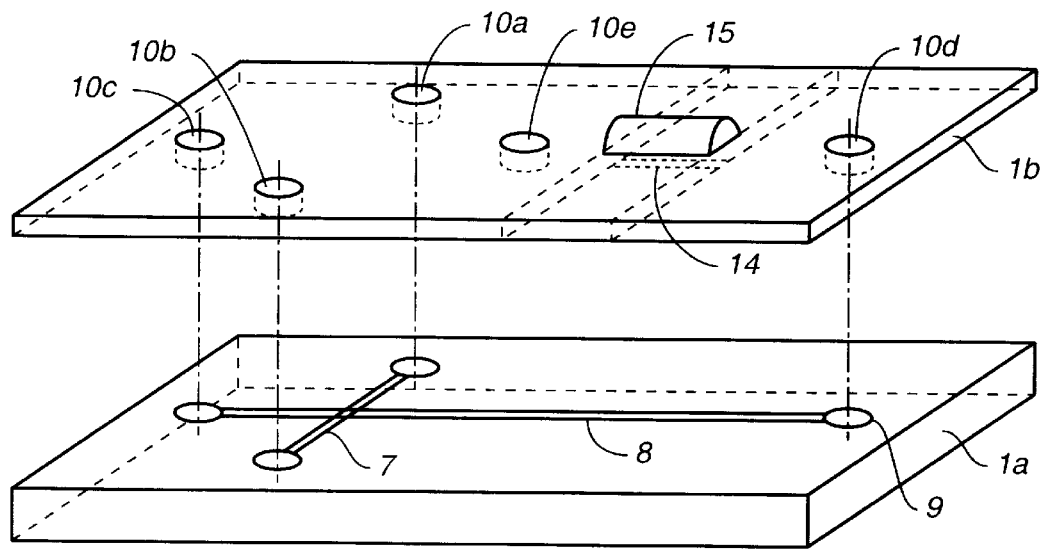
FIG._4A
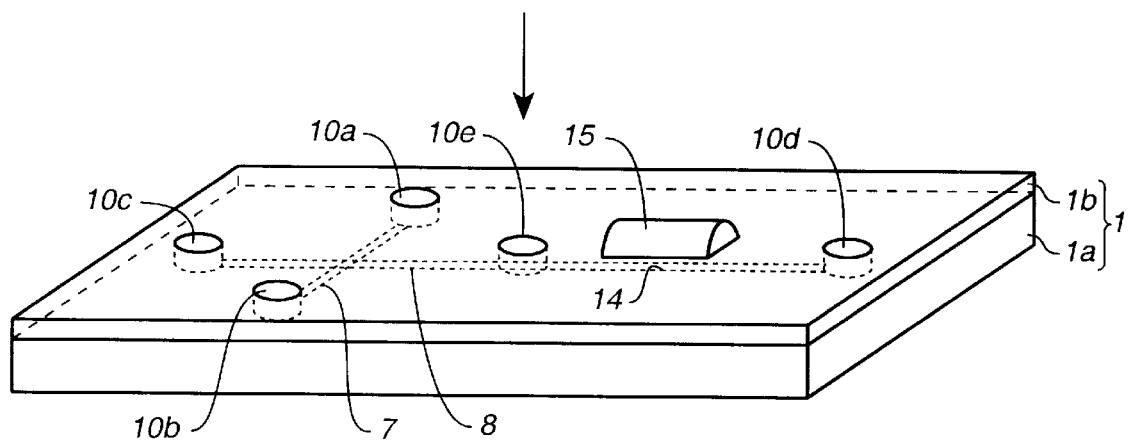
FIG._4B

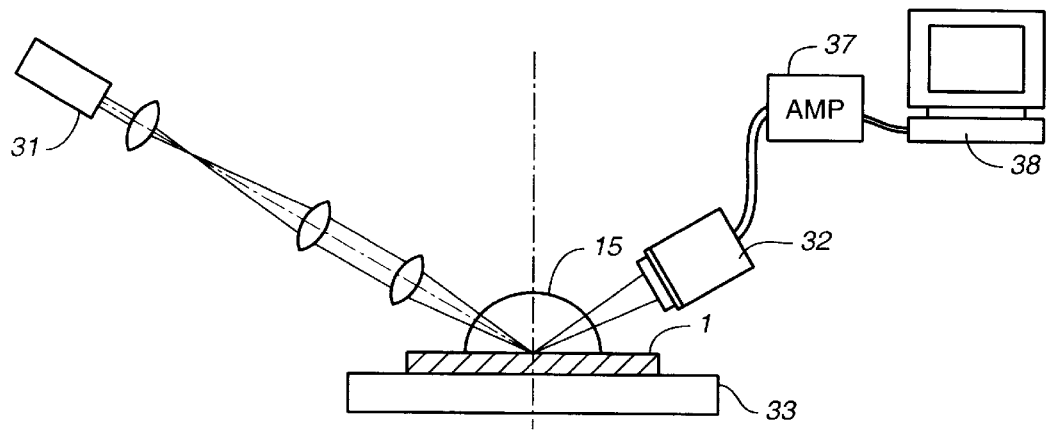
FIG._5A
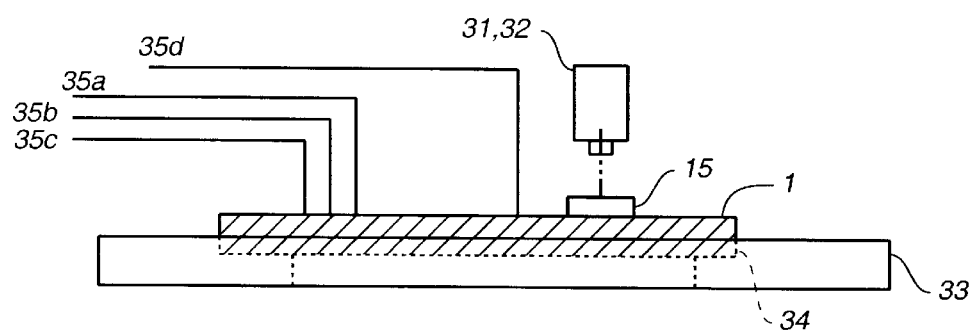
FIG._5B

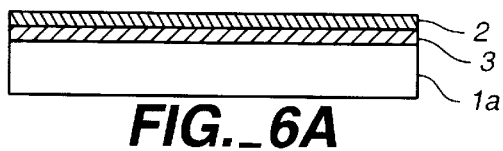
FIG._6A
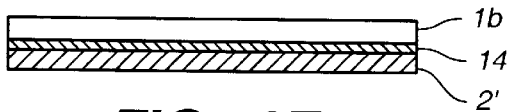
FIG._6E
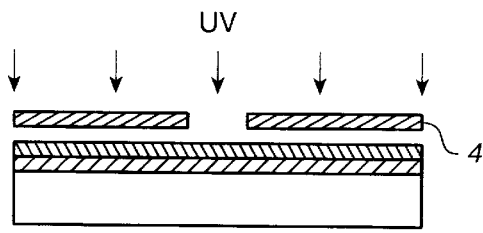
FIG._6B
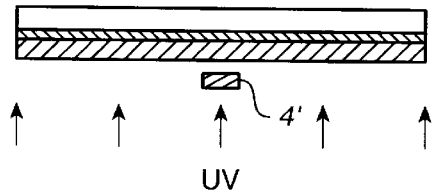
FIG._6F
FIG._6C
FIG._6G
FIG._6D
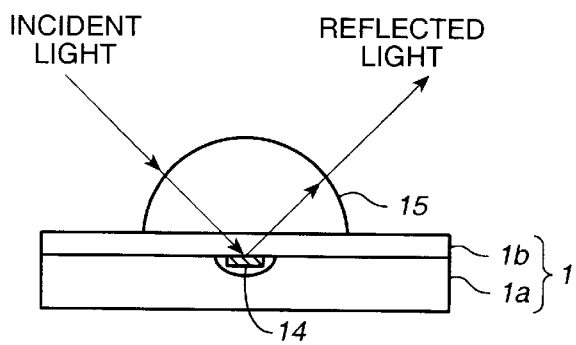
FIG._6H

DEVICE FOR ELECTROPHORESIS AND COMPONENT THEREFOR

This is a continuation-in-part of application Ser. No. 09/138,835 filed Aug. 24, 1998, now abandoned.

BACKGROUND OF THE INVENTION

This invention relates to a device for electrophoresis used for analyzing an extremely small quantity of protein or nucleic acid at a high speed and with a high resolution.

It has been known to analyze an extremely small quantity of protein or nucleic acid by electrophoresis, and a slab gel device has been a representative example of a device using this method of analysis. A slab gel device comprises a pair of glass slabs with the space therebetween filled with a gel to form a migration area. After a sample is injected at one end of the gel portion, a voltage difference of about 100V is applied at both its ends to cause the electrophoresis of the target substance for development. The developed target substance may then be detected by exposing the gel to a beam of laser light and measuring its absorption, by using a dye or by preliminarily labeling the target substance with a radioactive isotope and then using an auto-radiograph.

When a slab gel device is used, however, only a moderate voltage difference can be applied for analysis because the generation of Joule heat inside the gel presents a problem. For this reason, a long migration time from several hours to nearly 20 hours is required, and hence this cannot be considered a useful device when a quick analysis is required such as in a DNA analysis.

In view of the above, it is being proposed to make use of a capillary device for electrophoresis with a buffer filling the interior of a glass capillary having inner diameter of about 100 $\mu$m or less and a high voltage difference applied across its both ends after a sample has been injected at one end so as to cause the target substance to be developed inside the capillary. FIG. 1 shows a prior art example of such a capillary device for electrophoresis, having a glass capillary 20 with both of its ends immersed in a migration buffer 22a or 22b contained in a buffer tank 21a or 21b. Electrodes 23a and 23b, respectively connected to the plus and minus terminals of a high-voltage source 24 are immersed individually in these buffer tanks 21a and 21b. A detector 25 for detecting the target substance migrating inside the glass capillary 20 is disposed on one side of the capillary 20. The target substance is developed inside the glass capillary 20 and detected by applying a high voltage difference across the glass capillary 20 from the high voltage source 24 through the electrodes 23a and 23b and the buffer 22a and 22b. A device thus structured is useful because its surface area is large compared to the volume inside the glass capillary 20 and hence it can be cooled efficiently. Since the heat generated by the application of a high voltage can thus be radiated away quickly, a very small quantity of a DNA sample, for example, can be quickly analyzed with a high resolution by applying a high voltage.

Glass capillaries used in such a device for electrophoresis are not easy to handle when, for example, they are to be exchanged for replacement by the user since their outer diameter is as small as 10–100 $\mu$m and hence they are easily damaged. In view of the above, D. J. Harrison et al. proposed a planar capillary member formed by joining two planar substrates (Anal. Chim. Acta., 238 (1993) 361–366). FIG. 2 shows an example of such a planar capillary member having a first substrate 1a with a primary groove for analysis 8, a secondary groove for sample injection 7 and buffer tanks 9 formed thereon by a photo-fabrication technology and a second substrate 1b with throughholes 10 formed therethrough by a ultrasonic technology at positions corresponding to the buffer tanks 9. These two substrates 1a and 1b are joined together to form a planar capillary member.

When an analysis is carried out with such a planar capillary member, a buffer is introduced into the grooves 7 and 8 and a sample is injected from the buffer tank 9 at one end of the secondary groove 7. A high voltage is applied to the electrodes preliminarily provided on the inner walls and their neighborhoods of the throughholes 10 corresponding to the buffer tanks 9 at both ends of the secondary groove 7, thereby leading the sample by electrophoresis to the crossing point between the grooves 7 and 8. Thereafter, a high voltage is applied to the electrodes preliminarily provided on the inner walls and their neighborhoods of the throughholes 10 corresponding to the buffer tanks 9 at both ends of the primary groove 8 such that the target substance is developed therein. The developed target substance may be detected, for example, by applying a beam of laser light from outside and measuring its absorptivity.

Planar capillary members thus structured are not easily damaged because of their planar shape and are easier to handle than ordinary glass capillaries. With the detection method by light absorption by such a planar capillary device of electrophoresis, however, the sensitivity of detection becomes lower if the quantity of the sample is extremely small.

SUMMARY OF THE INVENTION

It is therefore an object of this invention to provide a planar capillary device with which an extremely small quantity of substance in the capillary can be measured with a high sensitivity.

A component of a device for electrophoresis embodying this invention, with which the above and other objects can be accomplished, may be characterized as comprising a pair of planar members such as glass substrates joined together one on top of the other such that a capillary is formed by a groove on the surface of at least one of these planar members, a metallic film on the inner wall of at least a portion of the capillary thus formed between the pair of planar members and a transparent prism disposed over this metallic film. A device embodying this invention for electrophoresis incorporating such a component may be characterized as additionally including electrodes inserted at selected positions in the capillary for providing a voltage difference between them, a light detector and a data processor. The light source is disposed to cause light to be made incident onto the metallic film at angles of incidence greater than the critical angle for total reflection, and the detector serves to detect reflected light. The data processor receives detection signals from the detector and obtains therefrom a resonance curve for optical excitation of surface plasmons on the metallic film. It also stores data on separation times of known components in electrophoresis for reference and serves to detect changes in the resonance curve to thereby analyze the components of a sample. The positions at which the electrodes are inserted are selected so as to prevent the metallic film provided inside the capillary from becoming dissolved or otherwise affected adversely by the voltages applied to the electrodes.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic structural diagram of a prior art device for electrophoresis;

FIG. 2 is a schematic exploded diagonal view of a component of a prior art planar capillary device for electrophoresis;

FIGS. 3A and 3B are diagrams for explaining the basic principle of detection according to this invention, FIG. 3A showing the Kretschmann distribution and FIG. 3B showing the relationship between the angle of incidence and the coefficient of refraction regarding the phenomenon of surface plasmons;

FIGS. 4A and 4B are diagonal views of a component of a device for electrophoresis embodying this invention respectively before and after its two substrates are joined together;

FIGS. 5A and 5B are respectively a front view and a side view of a device for electrophoresis embodying this invention, incorporating the component shown in FIGS. 4A and 4B;

FIGS. 6A, 6B, 6C, 6D, 6E, 6F, 6G and 6H are a series of sectional views of glass plates being processed to form the component shown in FIG. 4B.

Throughout herein, like or equivalent parts are indicated by the same numerals even where they are parts of different components or devices and may not necessarily be described repetitiously; and

DETAILED DESCRIPTION OF THE INVENTION

According to this invention, as explained above, a prism made of a transparent material with a high coefficient of refraction is disposed over a metallic thin film inside a portion of the inner wall of a capillary so as to thereby form a system for exciting surface plasmons ("the Kreischmann distribution"). The phenomenon of surface plasmon excitation will be explained next with reference to FIGS. 3A and 3B.

If a laser beam is made incident through a prism 15 onto a surface of a metallic thin film 16 contacting a sample 17, as shown in FIG. 3A, with an angle of incidence greater than the critical angle for total reflection, surface plasmons (compressional wave of electrons) are generated at the boundary between the metallic thin film 16 and the sample 17. When the parallel component (with respect to this boundary surface) of the wave-number vector of an incident light beam being made incident at a certain angle of incidence θ is equal to the wave number of the surface plasmon, there occurs the phenomenon of plasmon resonance, and the energy of the laser light is thereby transferred to the surface energy. As a result, the amount of reflected light is reduced, as shown in FIG. 3B. The angle of incidence θ at which the energy of the reflected light reaches a minimum is referred to as the resonance angle $\theta_{sp}$. The resonance angle $\theta_{sp}$ depends on the dielectric coefficient of the sample 17 below the metallic thin film 16 (or the sample density). The present invention is characterized as making use of the phenomenon of surface plasmons to detect changes in the concentration of an extremely small quantity of a target component developed through electrophoresis in a narrow groove for separation and analysis.

FIGS. 4A and 4B show an example of such a component member (or "the device component") embodying this invention, FIG. 4A showing the appearance before two glass substrates ("the first substrate 1a" and "the second substrate 1b") are joined together and FIG. 4b showing the appearance after they are joined to form a planar component for electrophoresis. The first substrate 1a has linear grooves ("the primary groove" 8 and "the secondary groove" 7, respectively for carrying out an analysis and for injecting a sample), and buffer tanks 9 formed on one of its surfaces. The grooves 8 and 7 and the tanks 9 are filled with a buffer for electrophoresis.

The second substrate 1b has throughholes 10a, 10b, 10c and 10d formed therethrough at positions which correspond to the buffer tanks 9. A thin metallic film 14 is formed on the surface of the second substrate 1b through which it contacts the first substrate 1a at a position corresponding to a selected portion of the primary groove 8, and a semi-cylindrical prism 15 is set on the other surface of the second substrate 1b at a position corresponding to (or opposite to) the thin metallic film 14. Another throughhole 10e is formed through the second substrate 1b between the prism 15 and the throughhole 10c on the side of the prism 15 with respect to the crossing point between the line connecting the throughholes 10a and 10b and the line connecting the throughholes 10c and 10d. Both the second glass substrate 1b and the prism 15 are made of a transparent material with a high coefficient of refraction.

FIGS. 5A and 5B show a device for electrophoresis incorporating the component described above (indicated generally by numeral 1) and including a laser light source 31 ("the light source"), which may be a He—Ne laser (of wavelength 632.8 nm), an Ar laser (of wavelength 488 nm) or a semiconductor laser (of wavelength several hundreds nm), set such that the light therefrom is made incident onto the surface of the thin metallic film 14, after passing through lenses, polarization plates (not shown) and the prism 15, at angles of incidence greater than the critical angle of total reflection. A photodiode or an array of photodiodes serving as a detector 32 is set on the optical path of the laser reflected by the metallic film 14 for detecting the reflected light. Optical components of known kinds for generally used for optical detection may be used for the purpose of this invention.

The component 1 is set on a fixed stage 33 provided with an indented portion 34 ("the positioning means") for appropriately positioning the component 1. Electrodes 35a and 35b are inserted respectively into throughholes 10a and 10b at both ends of the secondary groove 7 and electrodes 35c and 35d are inserted respectively into throughholes 10c and 10e along the primary groove 8 serving as flow routes formed inside the component 1 as described above with reference to FIGS. 4A and 4B for causing electrophoresis of a liquid sample by a voltage difference provided therethrough.

When an analysis is carried out, the grooves 7 and 8 are filled with a migration liquid and the component 1 is set inside the indented portion 34 of the stage 33. After a sample is injected through the throughhole 10a or 10b serving as a sample inlet, different voltages are applied to the electrodes 35a and 35b to cause the injected sample to migrate through the groove 7 for sample injection to the crossing point between the grooves 7 and 8. The light from the laser light source 31 is directed to a detection area of the component 1 (where the thin metallic film 14 is disposed) such that the reflected light from this thin metallic film 14 is received by the detector 32. A voltage difference is applied next between the electrodes 35c and 35d to cause the sample to migrate in the direction of the throughhole 10d and to become separated inside the primary groove 8, passing below the thin metallic film 14 and the prism 15. It is to be noted that the voltage difference along the primary groove 8 is applied only on the upstream side of the metallic film 14 because the detector 32 is disposed on the downstream side of the throughhole 10e with the electrode 35d inserted therein.

In the meantime, laser light with beams with angles of incidence within a finite range including a desired angle (resonance angle) of incidence is made incident from the source 31 as shown in FIG. 5A. The intensity of the corresponding reflected light from the metallic film 14 is detected by the detector 32, say, sequentially with a photodiode array, and the detected intensity is amplified by an amplifier 37 and then stored in a data processor 38 of a known kind. This may be accomplished by establishing a correspondence between angular components of the incident laser light with channel numbers of the photodiode array, and a resonance curve (showing the changes in the intensity of the reflected light according to the angle of reflection) can be obtained from such data. When a single photodiode is used as the detector 32, a resonance curve can be obtained similarly by varying the moving the laser light source 31 to vary the angle of incidence.

Components of a sample can be identified by causing the sample to migrate, detecting the separation times of the components by measuring the times when a change occurs in the resonance curve, and comparing them with separation time data for known components preliminarily stored in the data processor 38. The sample concentration can also be measured from the change in the resonance angle by comparing with a reference curve the resonance curve when the sample is caused to migrate. The change in the resonance curve may be stored by the data processor 38 either in terms of the shift in the resonance angle $\theta_{sp}$ or in terms of the change in the reflectivity at the wavelength of the incident light being used.

For obtaining a high theoretical plate number, it is preferable to reduce the beam size of the laser light. It is also preferable to automate the operations of the device described above after the component 1 is set inside the indented part 34 of the stage 33 and a sample is injected.

Next, a method of producing a planar device component for electrophoresis by the photo-fabrication technology is explained by way of an example. As shown in FIG. 6H, the device component 1 to be produced consists of a pair of glass substrates ("the first substrate" 1a and "the second substrate" 1b), the first substrate 1a having grooves formed on its surface for serving as flow routes and the second substrate 1b having the throughholes 10a, 10b, 10c, 10d and 10e formed therethrough and a metallic thin film vapor-deposited at portions of its surface at positions corresponding to the grooves on the first substrate 1a. These substrates 1a and 1b are produced by different processes. FIGS. 6A, 6B, 6C and 6D show a process for the production of the first substrate 1a. FIGS. 6E, 6F and 6G show a process for the production of the second substrate 1b.

By the photo-fabrication technology is meant the technology of making copies by transferring the pattern of a photo-mask, say, by coating the surface of a substrate with a photo-sensitive substance commonly referred to as a photo-resist or simply as a resist and exposing the surface to a light beam. A three-dimensional shape is obtained by etching or the like from a transferred planar pattern. No particular limitation is imposed on the kind of photo-resist to be used. Any kind of photo-resist is acceptable if it can withstand the etching process which follows. It should be thick enough to withstand such etching process to follow, the thickness being generally about several $\mu$m. For the exposure of the photo-resist to light, an exposure equipment commonly used for the production of semiconductor products such as an aligner or a stepper may be utilized.

For the production of the first substrate 1a of the device component 1 shown in FIG. 6H, a protective film 3 such as a Si film of several thousand Å in thickness for etching is formed on the glass substrate 1a as shown in FIG. 6A, say, by using a known kind of apparatus for sputtering or vapor deposition, and a resist 2 (such as AZ4620, a product of Hoechst Corporation) for patterning is formed on this protective film 3 by spin coating by using a spinner. The glass substrate 1a may comprise a glass material of various kinds, quartz or silicon and its thickness is preferably about 0.2–1 mm. No particular limitations are imposed on the material or the thickness of the protective film 3 as long as the film can withstand the etching process which follows. If the substrate 1a is a glass plate, a composite Au/Cr film (with thickness about 2000 Å/500 Å) with a Au film formed over a Cr film may be used. If the substrate 1a is a Si plate, a silicon nitrate film, a silicon oxide film or a composite of these films is desirable. In all these cases, the thickness is usually several thousand Å.

Next, an exposure apparatus is used to expose the resist 2 to UV light through a mask 4 for photolithography, and a desired patterned shape is obtained thereafter by development (FIG. 6B). The patterned resist 2 thus obtained is used next as a mask to pattern the protective film 3 (FIG. 6C). In the case of a Si film, a dry etching process may be carried out, for example, by using a mixed gas of $SF_6$ (20 sccm) and $O_2$ (5 sccm) in a vacuum of 20 mTorr. Other gases may be used for the dry etching process such as a gas obtained by adding Ar to a mixture of $CF_4$ and $CHF_3$ or to $SF_6$. As long as it is a kind of etching gas commonly used in this field of application, there is no particular limitation as to the choice. Next, the patterned resist 2 and protective film 3 are used as the mask and the glass plate 1a is etched, for example, with a water solution (about 46%) of hydrofluoric acid at a room temperature to form the grooves 7 and 8 as well as the buffer tanks 9 (FIG. 6D). The resist 2 and the protective film 3 are etched away thereafter.

If a silicon plate is used instead of the glass substrate 1a, capillary grooves can be formed thereon by a wet (anisotropic) etching method. An etching liquid of any kind commonly used in this field of application, such as a water solution of KOH, tetraethyl ammonium hydride and hydrazine, may be used for anisotropic etching. Such fine grooves may be formed on a silicon plate also by a dry etching method. Any gas commonly used for dry etching, such as a gas obtained by adding Ar to a mixture of $CF_4$ and $CHF_3$ or to $SF_6$, may be used as the process gas for the dry etching.

The second substrate 1b of the device component 1 shown in FIGS. 4A, 4B and 6H is obtained by forming tapered throughholes. Any method of forming throughholes through a plate of glass or quartz may be used for the purpose of this invention, but ultrasonic fabrication and sand blast fabrication methods are commonly used. The size of the throughholes does not particularly limit the scope of the invention but their open diameters are preferably about several hundred $\mu$m to several mm.

The metallic film 14 (say, of Au, Au/Cr with Cr below Au, Ag or Cu) is formed, for example, by using an apparatus for vapor deposition, and is coated with a resist 2' for patterning (such as aforementioned AZ4620) by using a spinner (FIG.

6E). The thickness of this metallic film 14 is generally about several hundred Å such that the reflectivity at the dip in the plasmon resonance curve approaches zero. Next, a mask 4' for photolithography is used as the resist 2' is exposed to UV light by means of an exposure apparatus (FIG. 6F) so as to be patterned by development in a desired shape. The metallic film 14 is then patterned by using the patterned resist 2' as the etching mask (FIG. 6G). If the metallic film 14 is gold, the etching may be carried out at a room temperature, for example, by using a mixture of 1.2 g of iodine, 3 g of ammonium iodide, 40 cc of water and 60 cc of alcohol.

It now goes without saying that other different methods may be used for the etching of the metallic film 14. It may be done, for example, by a lift-off method according to which the resist is first patterned, a metallic film is formed on this resist by vapor deposition, and the resist is thereafter removed. A film of silicon nitride or oxide may be further formed as a protective film on the surface of the metallic film 14.

The first substrate 1a and the second substrate 1b thus prepared are placed one on top of the other such that the flow route grooves and the metallic film are on the inside and are superposed together (FIG. 6H) and are heated together inside a vacuum oven at about 600° C. for several hours and then naturally cooled such that they are fused together. Thereafter, a prism 15 with a high coefficient of refraction (for example, of BK7, BaK4, F2 and LaK13) is pasted thereon, for example, through a liquid, paste or wax material with a coefficient of refraction close to that of the prism material. The prism 15 is a cylindrical body, having a length of several ten to several hundred μm in the direction of the groove and a cross-sectional shape of a semicircle or a triangle. The prism 15 may be attached to the glass substrate 1b alternatively by heating them together inside a vacuum oven at about 600° C. for several hours after the prism 15 is placed at an appropriate position on the glass substrate 1b and then cooling them naturally to fuse them together.

The electrodes 35a, 35b, 35c and 35d and contact pads for applying a potential difference to the migration liquid for electrophoresis may be formed on both surfaces of the second substrate 1b and on the inner surfaces of the throughholes before the two glass substrates 1a and 1b are joined together, for example, by sputtering Al through a metal mask to form films. The material for these electrodes and the contact pads does not limit the scope of the invention, as long as it can form films capable of withstanding the heat which is generated when the substrates 1a and 1b are joined together after these electrodes and the contact pads are formed. Materials for wiring generally used for the production of semiconductor devices, such as Au, Cu and Cr, may be used. Such materials can be used in a known kind of process such as vacuum vapor deposition and sputtering. The invention does not impose any limitation on the thickness of these electro-conductive films but it is usually several hundred to several thousand Å.

The invention has been described above with reference to only a limited number of examples but the disclosure is intended to be interpreted broadly. Many modifications and variations are possible within the scope of this invention. For example, although not separately illustrated, the throughholes and the grooves may be formed through and on the same one of the two substrates. The capillary flow route may be formed by first attaching a metallic film onto a prism and then covering a portion of a capillary-forming groove with the prism such that the metallic film thereon will contact the liquid inside the groove. In summary, since a component of a device for electrophoresis according to this invention has a metallic film formed along the flow route groove for analysis and a prism is set over the metallic film, optically excited surface plasmons can be used to detect components separated by electrophoresis. Thus, even if the amount of the sample is very small, various reactions, the speed of separation, contents of components of a sample and their concentrations can be accurately detected. Since the detector is positioned on the downstream side of the electrodes for applying a voltage difference, furthermore, the metallic film used as a part of the detector is not subjected thereto and is prevented from becoming dissolved thereby or otherwise affected thereby in any adverse manner.

What is claimed is:

1. A device component for electrophoresis, said device component comprising:

a pair of planar members, one of said planar members having a linear primary groove formed on a surface, the other of said planar members having throughholes formed therethrough at positions corresponding to two selected positions on said primary groove, said pair of planar members being joined together across said surface such that said groove forms a capillary with an inner wall of the other of said planar member;

a metallic film on said inner wall at a downstream position on said primary groove, both of said selected positions being on the same side of said downstream position; and a transparent prism disposed on an outer wall of one of said planar members corresponding to said downstream position of said metallic film.

2. The device component of claim 1 further comprising electrodes each inserted to a corresponding one of said throughholes.

3. The device component of claim 1 wherein said planar members are glass substrates.

4. The device component of claim 1 wherein one of said planar members also has a secondary groove formed thereon, said secondary groove transversely crossing said primary groove.

5. A device for electrophoresis comprising:

a device component which includes:

a pair of planar members, one of said planar members having a linear primary groove formed on a surface, the other of said planar members having throughholes formed therethrough at positions corresponding to two selected positions on said primary groove, said pair of planar members being joined together across said surface such that said groove forms a capillary with an inner wall of the other of said planar member;

a metallic film on said inner wall at a downstream position on said primary groove, both of said selected positions being on the same side of said downstream position; and a transparent prism disposed said metallic film; electrodes each inserted to a corresponding one of said throughholes, serving to provide a voltage difference therebetween;

a light source disposed such that light therefrom is made incident onto said metallic film through said prism at angles of incidence greater than a critical angle for total reflection;

a detector for detecting reflected light from said metallic film;

positioning means for positioning said device with respect to a fixed table; and a data processor for data-processing detection signals received from said detector.

6. The device of claim 5 wherein said device component further includes a secondary groove which transversely crosses said primary groove.

7. The device of claim 5 wherein said planar members are glass substrates.

8. The device of claim 5 wherein said light source serves to excite plasmons in said metallic film.

9. The device of claim 5 wherein said light from said light source serves is made incident onto said metallic film at angles of incidence in a range over the resonance angle for excitation of plasmons on a surface of said metallic film.

10. The device of claim 9 wherein said data processor stores data on separation times of known components in electrophoresis for reference.

11. The device of claim 9 wherein said data process serves to obtain a resonance curve of optical excitation of plasmons on the surface of said metallic film from said detection signals received from said detector.

12. The device of claim 11 wherein said data processor serves to detect a change in a resonance curve of optical excitation of plasmons on the surface of said metallic film.

13. The device of claim 12 wherein said detector includes an array of photodiodes and said data processor serves to sequentially read intensity of light received by said photodiodes to determine said resonance curve.

14. The device of claim 12 wherein said data processor detects said change from a shift in the resonance angle.

15. The device of claim 12 wherein said data processor detects said change from a change in reflectivity from said metallic film at a specified wavelength.

16. The device of claim 11 wherein said detector includes an array of photodiodes and said data processor serves to sequentially read intensity of light received by said photodiodes to determine said resonance curve.

17. The device of claim 9 wherein said data processor serves to detect a change in a resonance curve of optical excitation of plasmons on the surface of said metallic film.

18. The device of claim 17 wherein said detector includes an array of photodiodes and said data processor serves to sequentially read intensity of light received by said photodiodes to determine said resonance curve.

* * * * *